United States Patent [19]

Anapliotis

[11] Patent Number: 4,934,354
[45] Date of Patent: Jun. 19, 1990

[54] DEVICE FOR EXTERNALLY FIXING AND/OR IMPARTING TRACTION TO THE CERVICAL SPINE

[75] Inventor: Emmanuel Anapliotis, Berlin, Fed. Rep. of Germany

[73] Assignee: MECRON Medizinishche Produkte GmbH, Berlin, Fed. Rep. of Germany

[21] Appl. No.: 184,307

[22] Filed: Apr. 21, 1988

[30] Foreign Application Priority Data

Apr. 21, 1987 [DE] Fed. Rep. of Germany ... 8705922[U]

[51] Int. Cl.$^5$ .............................................. A61F 5/00
[52] U.S. Cl. ......................................... 128/75; 128/69
[58] Field of Search .................... 128/75, 76 R, 87 B, 128/84 R, 89 R, 89 A, 78, 69

[56] References Cited

U.S. PATENT DOCUMENTS

| 2,712,820 | 7/1955 | Robinson . | |
| 2,820,455 | 1/1958 | Hall | 128/87 |
| 3,669,102 | 6/1972 | Harris | 128/84 R |
| 3,957,040 | 5/1976 | Calabrese . | |
| 4,541,421 | 9/1985 | Iversen et al. | 128/87 B |
| 4,620,530 | 11/1986 | Lanier et al. . | |
| 4,735,196 | 4/1988 | Krag | 128/75 |

FOREIGN PATENT DOCUMENTS

| 2637244 | 6/1977 | Fed. Rep. of Germany . |
| 3302078 | 7/1984 | Fed. Rep. of Germany . |
| 2405063 | 4/1979 | France . |
| 2576774 | 8/1986 | France . |

Primary Examiner—Edgar S. Burr
Assistant Examiner—Huong Q. Pham
Attorney, Agent, or Firm—Spencer & Frank

[57] ABSTRACT

Device for externally fixing and/or imparting traction to the cervical spine having a fastening ring attached to the patient's head, the ring having plural outwardly projecting fastening bearings. A plurality of support bearing are affixed to the chest and/or back of the patient and the fastening and support bearing are connected together by plural connecting rods. The connecting and support bearings include clamping elements and ball joints which are connected to the connecting rods by the clamping elements. The ball joints are preferably composed of a pin having a spherical head. The fastening ring includes a bore having an internal thread, the pin having a reduced diameter at its end opposite the spherical head, the pin having an external thread which is threadable into the corresponding internal thread of the bore.

9 Claims, 2 Drawing Sheets

DEVICE FOR EXTERNALLY FIXING AND/OR IMPARTING TRACTION TO THE CERVICAL SPINE

BACKGROUND OF THE INVENTION

1. Field of the Invention

The invention relates to a device for externally fixing and/or imparting traction to the cervical spine and including a fastening ring attached to the patient's head and a plurality of outwardly projecting fastening bearings, a plurality of support bearings attached in the patient's chest and/or back region and a plurality of connecting rods which connect the fastening and support bearings and are provided with connecting and support bearing ball joints which are connected with the connecting rods by means of clamping elements.

2. Brief Description of the Prior Art

A device of the abovedescribed type is known and is employed, for example, to attach a fixing and traction-imparting halo used in the treatment of diseases of the cervical spine. The device includes a fastening ring which is attached to the patient's head at the level of the forehead and is provided with a plurality of bores for receiving pressure plates disposed between the patient's head and the fastening ring and for receiving laterally outwardly projecting fastening bearings. In the patient's chest and/or back region, support bearings are attached preferably to a supporting bandage or a supporting vest pulled over the upper body of the patient to be treated and are connected with the fastening bearings at the fastening ring by connecting rods. These connecting rods may be adjustable in length so that, if required, the cervical spine can be fixed as well as put into traction.

Customarily, the fastening bearings are composed of conical pins which project horizontally from the fastening rings while the support bearings are composed of cylindrical pins projecting vertically from corresponding fastening plates. The connection between the connecting rods and the fastening bearings and the support bearings is effected by two clamps which are rotatable opposite to one another in order to equalize the sides and receive, on the one hand, the pin of the fastening or support bearing and, on the other hand, the respective connecting rod, while, after aligning the device and applying the necessary traction force, they connect the rods and pins together in a force-locking manner.

Although the mutually oppositely rotatable clamps for producing the force-locking connection between the pins of the fastening and support bearings on the one hand and the connecting rods on the other hand provide for a sloped connection between the fastening bearings and the support bearings, their structure is complicated and thus expensive and, due to their limited adjustability, the treating physician has difficulties in adjusting them and aligning them in such a manner that no bending stresses act on the connecting rods which would be disadvantageous for the patient.

SUMMARY OF THE INVENTION

It is an object of the present invention to provide a device of the above-mentioned type which is distinguished by a simple configuration as well as ease of adjustment and alignment.

This is accomplished by the present invention by providing the fastening and support bearings with ball joints which are connected to the connecting rods by means of clamping elements.

The ball joints, composed of a pin having a spherical head, when used as fastening bearings, may have a reduced diameter at their end opposite the spherical head and may be provided with an external thread which is screwed into the corresponding internal thread of a bore in the fastening ring, the external threaded portion of the fastening bearing and the internally threaded bore of the ring forming corresponding attachment means for securing the bearing to the ring. In the alternative, other attachment means could be provided for securing the ring and the bearings. If used as a support bearing ball joint, the ball joints may be arranged in the center of and in vertical orientation on a plate provided with bores for fastening to a supporting bandage or to a supporting vest.

The solution according to the invention is distinguished by a simple construction and affords the treating physician easy adjustability and alignment of the device for externally fixing and/or imparting traction to the cervical spine.

An advantageous embodiment of the solution according to the invention is characterized in that the clamping element includes a ball socket which is elastically widenable so as to receive a ball joint and a bore for the passage of a connecting rod as well as an internal thread disposed between the ball socket and the bore into which a screw can be screwed to establish a force-locking connection between the ball joint, the clamping element and the connecting rod, with the screw preferably being a hexagon socket screw.

This configuration of the solution according to the invention enables the treating physician to attach the fastening ring to the patient's head and to apply the supporting bandage or supporting vest to the patient's upper body and to loosely connect the fastening and support bearing by way of the connecting rods. After precisely aligning the clamping elements and the connecting rods, a firm connection can be established by tightening the screws in the internal threads of the clamping elements, thus accurately adjusting the device in a manner which is precisely adapted to the patient. In particular, any angular position can be established in this way so that optimum fixation can be performed and, if necessary, the cervical spine of the patient can also be subjected to traction.

BRIEF DESCRIPTION OF THE DRAWINGS

The idea on which the invention is based will be described in greater detail with reference to an embodiment that is illustrated in the drawing figures. It is shown in:

FIGS. 1 and 2 are schematic representations of a device attached to the upper body of a patient for externally fixing and/or imparting traction to the cervical spine attached for treatment of diseases of the cervical spine and for the attachment of a halo. In both views, as well as in the detail views of FIGS. 3 and 4, the same reference numerals identify the same components.

Figure 1:
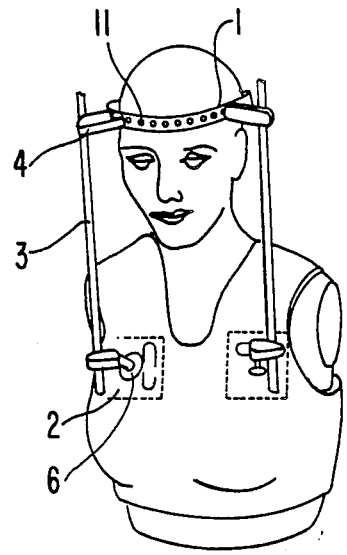
FIG. 1 is a schematic representation, as a front view, of a patient wearing the device for externally fixing and/or imparting traction to the cervical spine.
Figure 2:
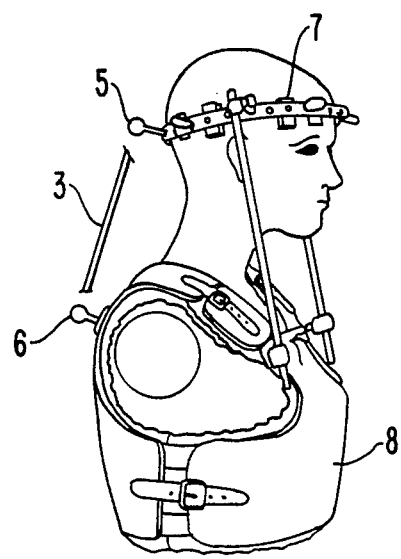
FIG. 2 is a side view of the applied device of FIG. 1.

The device for externally fixing and/or imparting traction to the cervical spine includes a fastening ring 1 which is attached to the patient's head at the level of his forehead and is provided with bores 11 distributed over its circumference for receiving pressure plates 7 oriented inwardly toward the patient's head and with outwardly oriented fastening bearings. Depending on the type of disease the patient has and the type of treatment selected, two or four supports are provided. To provide support, i.e. for fixation or traction, supporting plates 2 are provided in the patient's chest or back region which plates are connected through bores, if necessary, with a supporting bandage or a supporting vest 8 placed around the patient's upper body. In their centers, supporting plates 2 are provided with perpendicularly projecting ball joints 6 which, similarly to ball joints 5 that are attached to fastening ring 1, can best be seen in the illustration of FIG. 2 where, in order to more clearly show the ball joints, the connection between fastening and support bearings is shown as being interrupted.

The connection between fastening bearings 5 and support bearings 6 is effected by way of connecting rods 3 and clamping elements 4 which, after all supporting connections have been adjusted, are connected with one another in a force-locking manner.

Figure 3:
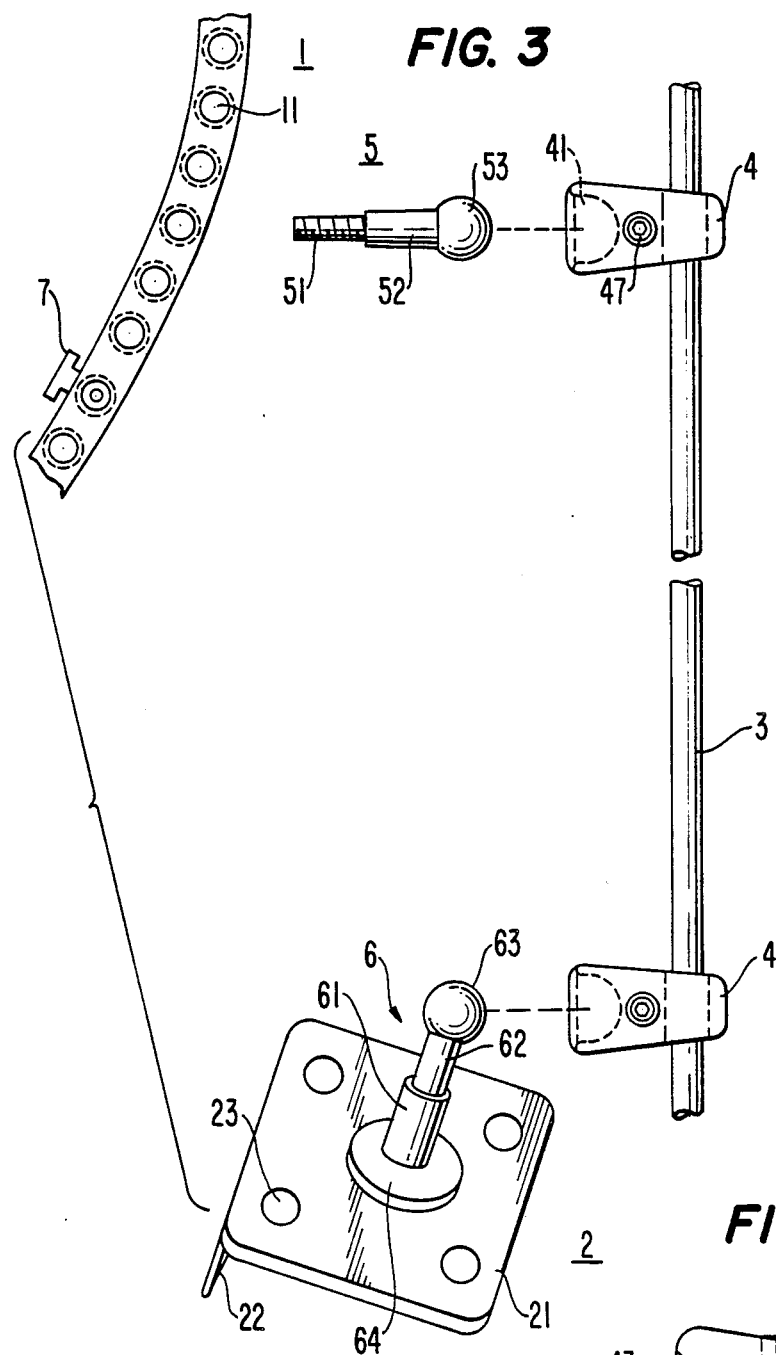
FIG. 3 is an exploded view showing the details of the device according to FIGS. 1 and 2.

The exploded view of FIG. 3 shows details of the device for externally fixing and/or imparting traction to the cervical spine.

FIG. 3 shows, at the top left, a sectional view of a fastening ring 1 which includes a plurality of bores 11 to accommodate pressure plates 7 and ball joints 5. The pressure plates 7 and ball joints 5 can be connected, respectively with fastening ring 1 by inserting pressure plates 7 or ball joints 5, respectively in a precise fit into the bores 11 of fastening ring 1 or by screwing in the respective pressure plates 7 and/or ball joints 5.

In the embodiment shown herein, ball joint 5 includes a cylindrical pin 51, 52 which is provided with an extension and, at its lower end, with an external thread (as shown in FIG. 3). At its other end, ball joint 5 is provided with a spherical head 53.

Support bearing 2 includes an essentially rectangular or square plate 21 which is provided with an angled side 22. Plate 21 is provided with a plurality of bores 23 which serve for fastening to a supporting bandage or a supporting vest. In its center, plate 21 is provided with a ball joint 6 which perpendicularly projects therefrom and is composed of a cylindrical pin 61, 62 and a spherical head 63. Cylindrical pin 61, 62 is provided with an extension and is seated in the center of a circular plate 64 which is likewise seated in the center of plate 21.

Figure 4:
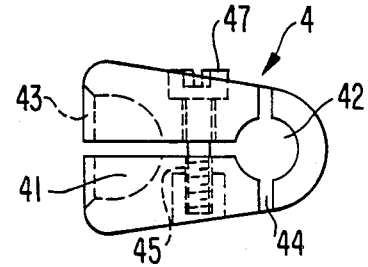
FIG. 4 is a detail view of the clamping element.

Spherical heads 53, 63 of ball joints 5, 6 are received by the elastically widenable ball socket 41 of each clamping element 4 which is provided with a bore 42 through which a connecting rod 3 is placed. As can be seen particularly well in the detail view of the clamping element 4 in FIG. 4, clamping element 4 is provided with slits 43, 44 which serve, by elastically widening, to accommodate spherical heads 53, 63 and connecting rod 3, respectively. Between ball socket 41 and bore 42, an internal thread 45 is provided into which a screw, preferably a hexagon socket screw 47, can be screwed.

To attach the device for externally fixing and/or imparting traction to the cervical spine, the fastening ring 1 is placed around the patient's head and the supporting bandage or supporting vest 8 is placed on the patient's upper body together with support bearings 2 attached thereto. The clamping elements 4 which are displaceable on connecting rods 3 and are equipped with ball sockets 41 placed over spherical heads 53, 63 and the entire system are accurately aligned, given a slight tension by way of hexagon socket screw 47, i.e. a slight clamping effect, with respect to the connection of spherical head 53, 63 in its respective ball socket 41 and in bores 42 relative to connecting rod 3 so that, for example, all connections are arranged in symmetry and thus symmetrical fixation and traction are produced. After the precise adjustment, hexagon socket screws 47 are tightened and thus produce a reliable, firm, force-locking connection between fastening ring 1 and support bearings 2.

If it should become necessary to subsequently make a correction, the clamping elements to be corrected can be easily loosened and re-aligned.

The above-described invention is not limited to the illustrated embodiments and can be modified and supplemented in many ways. For example, it is possible to provide a fixed connection between clamping elements 4 and a connecting rod 3, with such connecting rod 3 being composed of two rods which can be adjusted relative to one another.

I claim:

1. Device for externally fixing and/or imparting traction to the cervical spine of a patient comprising:
   a plurality of detachable fastening bearings each of said bearings including a ball joint means, said ball joint means including a pin having a spherical head;
   a fastening ring for being attached to the patient's head;
   a plurality of attachment means defining a part of and spaced circumferentially about said ring for selective attachment and positioning of each of said detachable fastening bearings independent of the selective positioning of the other detachable fastening bearings, and each fastening bearing having a first end for attachment to one of said attachment means;
   a plurality of support bearings for being applied in one of the chest or back region of the patient;
   a plurality of connecting rods for connecting the fastening and support bearings; and
   clamping elements connected to and longitudinally displaceable along said connecting rods, said clamping elements including means connected to said ball joint means for articulatably connecting each of said connecting rods to one pair of said fastening and support bearings.

2. Device according to claim 1, wherein said attachment means includes a bore having an internal thread and said pin has a reduced diameter at its end opposite its spherical head and is provided with an external thread threadable into the corresponding internal thread of said bore.

3. Device according to claim 1, further including a plate provided with bores for fastening each said support bearing to a supporting vest means, wherein said support bearings include a ball joint at a first end, a second end of each said support bearings is disposed in the center of said plate, and said ball joint extends and is separated from said plate.

4. Device according to claim 1, wherein said clamping element includes an elastically widenable ball socket for receiving said ball joint means and a bore for the passage of said connecting rod as well as an internal thread disposed between the ball socket and the bore for receiving a screw to produce a force-locking connection between said ball joint means, said clamping element and said connecting rod and said screw.

5. Device according to claim 4, wherein said screw is a hexagon socket screw.

6. Device according to claim 2, wherein said clamping element includes an elastically widenable ball socket to accommodate said ball joint means and a bore for the passage of said connecting rod as well as an internal thread disposed between said ball socket and the bore for receiving a screw to produce a force-locking connection between said ball joint means, said clamping element and said connecting rod.

7. Device according to claim 6, wherein said screw is a hexagon socket screw.

8. Device according to claim 3, wherein said clamping element includes an elastically widenable ball socket to accommodate said ball joint means and a bore for the passage of said connecting rod as well as an internal thread disposed between said ball socket and the bore for receiving a screw to produce a force-locking connection between said ball joint means, said clamping element and said connecting rod.

9. Device according to claim 8, wherein said screw is a hexagon socket screw.

* * * * *